United States Patent [19]

Charatan

[11] Patent Number: 4,836,227
[45] Date of Patent: Jun. 6, 1989

[54] ORAL HYGIENE DEVICE

[76] Inventor: Norman Charatan, 22 Varady Dr., Fords, N.J. 08863

[21] Appl. No.: 79,694

[22] Filed: Jul. 30, 1987

[51] Int. Cl.$^4$ ............................................. A61C 15/04
[52] U.S. Cl. ..................................... 132/324; 132/321
[58] Field of Search ..................................... 132/89–93; 401/134

[56] References Cited

U.S. PATENT DOCUMENTS

| | | | |
|---|---|---|---|
| 2,981,264 | 4/1961 | DeFelice | 132/91 |
| 3,696,821 | 10/1972 | Adams, IV | 132/91 |
| 4,019,522 | 4/1977 | Elbreder | 132/90 |
| 4,519,408 | 5/1985 | Charatran | 132/89 |
| 4,633,892 | 1/1987 | Charatran | 132/89 |

Primary Examiner—Albert J. Makay
Assistant Examiner—Allen J. Flanigan
Attorney, Agent, or Firm—Robert D. Farkas

[57] ABSTRACT

An oral hygiene device is comprised of a hollow housing having a weakened section in the periphery of the housing so that when the weakened section is broken, a user may grasp and separate the housing into two portions. A length of stretchable dental material and dentifrice is totally encased within a cavity in the unbroken housing and is secured at each end to two interior regions of the housing that can be separated at the weakened section. The length of the dental material is sufficient to allow the two portions of the housing to be grasped with opposite hands of the user and disposed in spaced apart relationship with each other, thereby permitting a portion of the dental material to be stretched uniformly in cross-section, by passing the dental material through small draw-like openings in each end of the housing so as to form a uniform and smooth exposed length of dental material and a quantity of the dentifrice which may be applied between adjacent teeth of the user, in conventional fashion. Dentifrices, such as medicaments, flavors, and antiseptics, stored within the cavity of the unbroken housing are dispensed when the dental material is dispensed outwardly from the draw-like openings for application by the user.

2 Claims, 3 Drawing Sheets

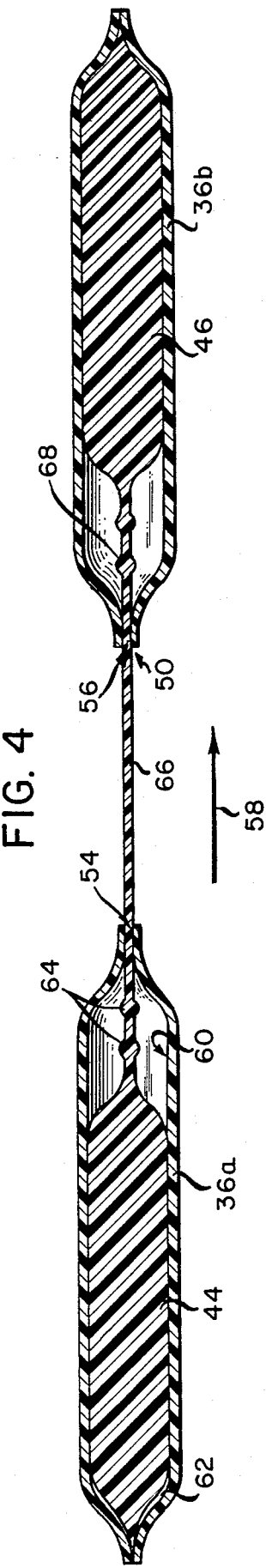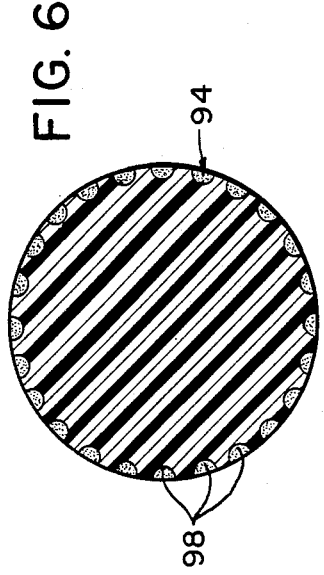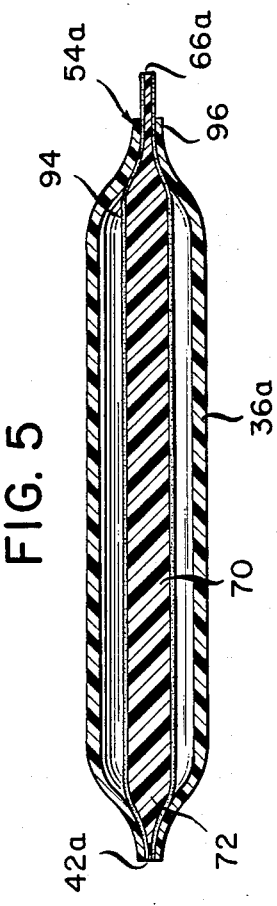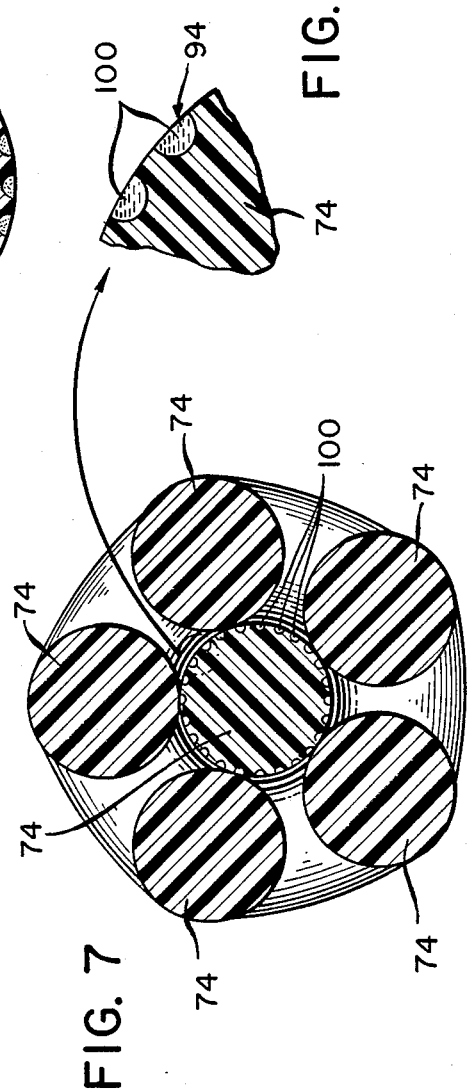

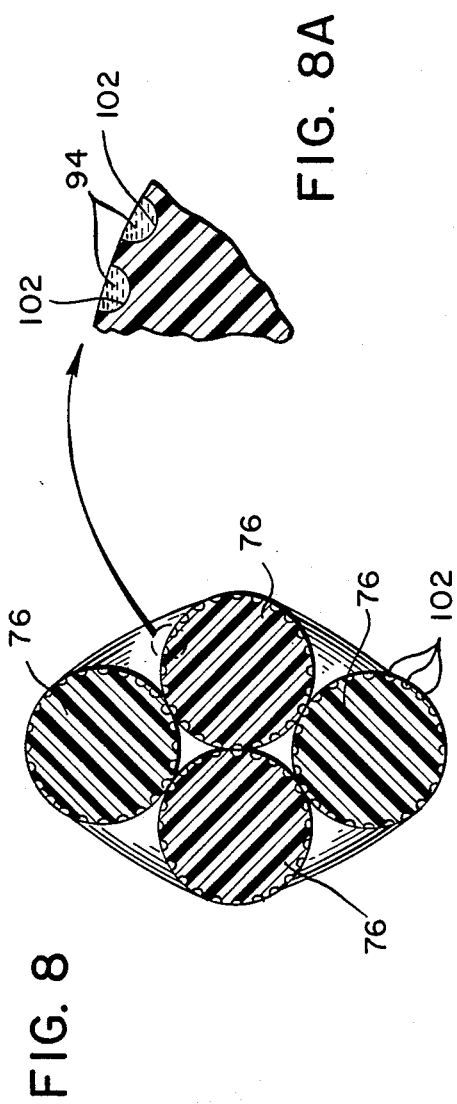
FIG. 8
FIG. 8A
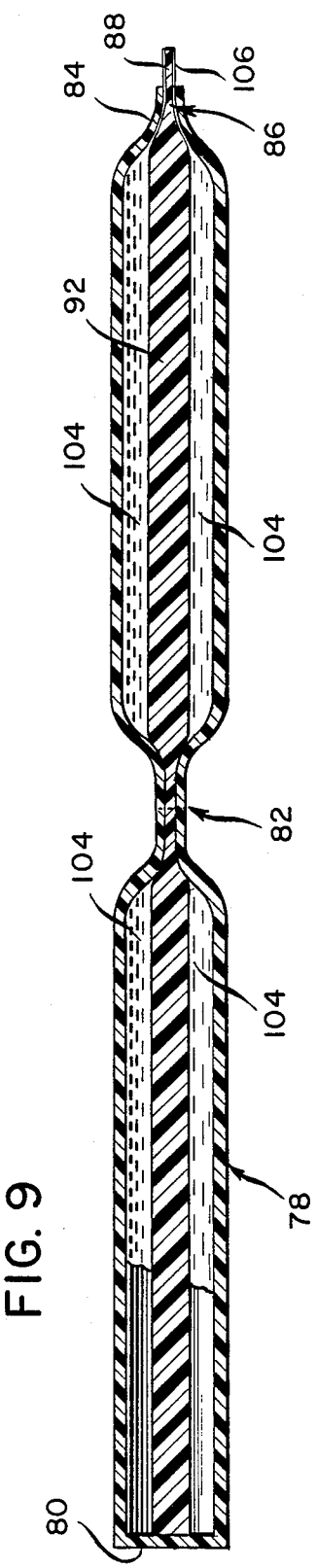
FIG. 9

ORAL HYGIENE DEVICE

BACKGROUND OF THE INVENTION

1. Field of the Invention

This invention concerns dental floss-like apparatuses and dentifrice containers and the manner in which they are constructed for use in preventative and corrective dental care. This invention further concerns dental floss-like containers, of the one-time use variety, serving also as handles by which the user may manipulate and use the device.

2. Description of the Prior Art

The prior art abounds with devices which concern the use of dental floss. U.S. Pat. No. 2,982,264, issued Apr. 25, 1961, by A. F. DeFelice, teaches a dental cleaner massager, wherein such massager utilizes a floss member of conventional construction, secured to the apex of two cone-like shaped bodies fabricated from an elastomeric rubber-like material. In use, the length of the dental floss, extending between the apex of the cones, pass between the teeth of the user so as to permit the tapered sharp cone to enter into the space between the teeth, further enhancing the cleaning process and providing for massaging. The cones act as handles for the apparatus. In use, the De Felice device requires a container to house a portion of the dental floss to be applied to the teeth, and presumptively, at least portions of one of the cones that may come in contact with the mouth of the user for sanitary purposes. No dentifrice is employed.

In like fashion, U.S. Pat. No. 2,443,415, issued June 15, 1948 to J. Buscarino describes a dental floss holder, which holder has a finger grasping portion and an anvil affixed thereto. Affixed to the anvil is a length of dental floss which is pre-stretched and defined as to its length. No dentifrice is described.

U.S. Pat. No. 3,696,821 issued Oct. 10, 1972 to John Q. Adams, IV, discloses a pair of caps or thimbles that engage over the fingers of the user, the closed ends of the thimbles being apertured to allow feeding of a simple dental floss therethrough, from a supply container to the length that is required to clean teeth. In use, the thimbles functionally clamp the dental floss to the fingers so that the floss may be properly tensioned for use without the inconvenience and frequent discomfort which arises when the dental floss is wound around the fingertips, in convention fashion. No dentifrice is described.

U.S. Pat. Nos. 4,519,408, issued Apr. 28, 1985, and 4,633,892, issued Jan. 6, 1987, to me, teach a dental floss-like apparatus which utilizes a frangible tube, sealed at both ends, containing therewithin an elastomeric-like material that—once stretched—will not resume its original unstretched length or condition. As the elastomeric-like material stretches, its cross-sectional dimensions decrease so as to manifest an elongated monofilament between the broken ends of the housing, which monofilament-like material can be used to effectively clean the teeth, whilst the proximal handles may be grasped by the user in a convenient fashion. However, the difficulties encountered with the type of manufacture taught by U.S. Pat. No. 4,519,408 is that the elongated material, disposed between the two broken handle-like ends of the unitary housing, sometimes manifest uneven cross-sections, along its exposed length. This is due to the inability to mix the material properly and to uniformly extrude same so as to adhere uniformly to the interior walls of the housing so as to insure a uniform stretching process. A manufacturing technique used to practice my invention under U.S. Pat. No. 4,519,408 is the co-axial simultaneous extrusion of the inner, elastomeric-like material and the outer rigid housing. My later U.S. Pat. No. 4,633,892 teaches the use of two draw-like small openings to insure a uniform cross-section of the extrudate. Neither of my prior two Patents teaches the use of any dentifrice material stored within the housing, dispensed when the housing is broken.

In all of the above described disclosures, no teaching illustrates an apparatus in which the housing may be broken apart, serving as handles for the manual grasping use, and provides for an elongated plastic-like material which extends between the broken ends, such material having a worked and uniform cross-section throughout its length, carrying a dentifrice on or about the elongated plastic-like material.

SUMMARY OF THE INVENTION

The present invention overcomes the problems posed by the prior art and succeeds in accomplishing the objects hereinabove set forth by providing a housing, each of the two ends of the housing being closed. Such housing contains therewithin a length of material, of the elastomeric-like variety, which material is extensible and which material will not revert back to its original form or length once it is extended, and which material may be disposed to fill part or all of the entire cavity comprising the intact housing, such that when the housing is broken at its weakened central area, a small opening, in each opposed broken portion, having a dimension smaller than the inner cross-section of the housing, acts as a drawing bar through which the elastomeric-like material may be drawn and uniformly thinned out so as to provide a uniform cross-section elongated dental floss-like material of a particular cross-section shape and size. Dentifrice-like agents, be they liquid, powder, gels or paste, are dispensed from the interior of the housing when the elongated dental floss-like material is exposed for use and are safely stored within the cavity prior to its being broken.

One of the objects of the present invention is a one-time use dentifrice-carrying dental flossing device which does not require manual manipulation of the dental floss-like material, as by contacting same with the user's hand, prior to its use.

Another object of the present invention is a dentifrice-carrying dental floss-like housing which housing maintains the flossing material in a clean, safe and undisturbed condition following its initial manufacture, which permits the user to easily and quickly make a clean dental floss-like material readily available for use.

Still another object of the present invention is an inexpensive dentifrice storage device, using a dental flossing device which in of itself, may be carried about, from place to place, such that the integrity of the cleanliness of the dental floss and dentifrice is not harmed prior to the time in which the user elects to utilize same.

Yet another object of the present invention is a dentifrice and dental flossing device which is simple to manufacture, convenient in its use, rugged in its construction, and which may bear advertising or other descriptive material directly thereupon.

A further object of the present invention is overcoming the objectional concept of requiring users to put their fingers into their mouths when utilizing a dental floss-like device.

Still yet another object of the present invention is avoiding the need for the user to wind the dental floss about their fingers, prior to the use thereof.

Still a further object of the present invention is utilizing a dental floss-like material which reaches a uniform cross-section at its elongated length, which will not extend further, whilst having a uniform cross-section throughout its exposed length, thereby making it more convenient to utilize the apparatus.

Yet another object of the present invention is a dental floss device which dispenses dentifrice and dental floss-like material, without spoilage or evaporation prior to use.

These objects as well as other objects of the present invention, will become still more readily apparent after reading the following description of the accompanying drawings.

BRIEF DESCRIPTION OF THE DRAWINGS

FIG. 4 is a side elevation, cross-sectional view of the apparatus shown in FIG. 3 in its extended form.

FIG. 5 is another embodiment of a portion of the apparatus shown in FIG. 3, in side elevation, cross-sectional view.

FIG. 6 is an enlarged view of a portion of the apparatus shown in FIG. 5 shown in side elevation cross-sectional view.

FIGS. 7 & 7A are another embodiment of the side elevation, cross-sectional view of the apparatus shown viewed in FIG. 5.

FIGS. 8 & 8A are still another embodiment of the side elevation cross-sectional view of the apparatus shown viewed in FIG. 5.

FIG. 9 is still another embodiment shown in side elevation, cross-sectional view, of the present invention, shown in cross-sectional view.

DESCRIPTION OF THE PREFERRED EMBODIMENT

Figure 1:
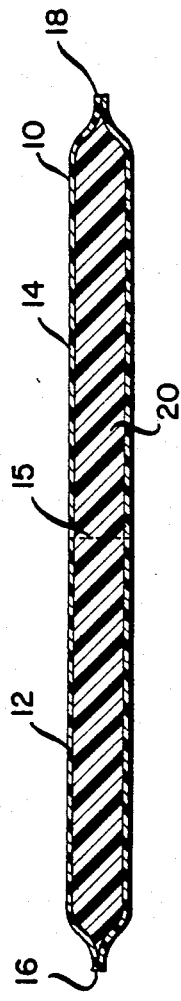
FIG. 1 is a side elevation, cross-sectional view of an embodiment of the present invention.

The structure and method of fabrication of the present invention is applicable to a housing, said housing preferably fabricated from a right angle cylinder. The housing may be constructed from a plastic material, such plastic material being rigid or semi-rigid polyethylene, polypropylene, or the like, said housing contains a dentifrice and is constructed to be impervious to same when unbroken. The housing may be transparent or opaque—as desired. The housing should have a length of approximately an inch and a half to three and a half inches, with a diameter of approximately one-sixteenth of an inch to three-sixteenths of an inch, O.D. The central regions of the housing, approximately mid-way between its two ends, should be deformed so as to define a depression therein extending radially inwardly from its outermost walls. Disposed within a cavity formed by the housing is an elastomeric-like material, such as ethylene propylene copolymer, such as VISTA-LON 404, manufactured by Exxon Chemical Co. of Houston, Tex., U.S.A., or ethylene-vinyl acetate copolymers, such as ELVAX, a product of the Dupont Company, Wilmington, Del., U.S.A., or low density polyethylene elastomer compounds, equivalent to HEISLER COMPOUND HC5201, a product of HEISLER COMPOUNDING Division, Container Corporation of America, Wilmington, Del., U.S.A. Such materials are noted to have a capability of being manually extensible when opposing forces are applied at opposite ends of its length. A dentifrice is also disposed within the housing. At some point in the stretching process, such tended exposed material reaches a maximum length, having then a foreshortened diameter. The ability to continuously stretch such material is limited, such that the material achieves a much greater tensile strength at the time it reaches its maximum elongation, greater than its original tensile strength. The same material will not revert back to its original thicker configuration when the tensioning forces are released. I have fabricated test samples of these materials and note that such materials tend to remain adhered to the interior of completely filled plastic housings, in the regions adjacent the closed ends of the cylindrical housing, yet tend to stretch thinner in the central region adjacent to the weakened and broken portion of the housing. No adhesive is absolutely required to secure these stretchable elastomeric-like materials to the interior of any rigid housing, since the stretched portions thereof reach a maximum tensile strength point, prior to the time that the remaining unextended elastomeric-like material, attached to the housing portion, is separated away from the interior wall of each housing portion. In addition, when a housing having a rectangular cross-section is utilized, the central material will substantially produce a rectangular cross-section. In all cases, the ends of the central elastomeric-like material, having an equal or slightly smaller diameter than the internal diameter of the cavity, are secured to the sealed ends of each portion of the housing, which are disposed furthestmost from each other or are sealed at a point in each housing end, intermediate the draw hole and the closed end. In order to prevent slubbing, or the generation of non-uniform cross- sectional protuberences, and to increase tensile strength prior to a full extention of the elongatable material, one drawhole of relatively small diameter is formed adjacent each of the two broken opposed ends of the housing, compelling any slubs, generated within the housing—to be further drawn down and to provide a cross-section of stronger extended material which is uniform and of lesser cross sectional dimensions, and to control the dispensing of the dentifrice. Passing the elongatable material through the draw holes will cause some cross-linking and hence, an increased degree of tensile strength and a decrease in the further ability to stretch. As desired, dentifrice-like materials, such as flavorings, flourides and antiseptic materials may be admixed with the extrudate and allowed to admix or attach to the elastomeric material prior to its use. The well-known process of surface bonding provides "cells" into which dentifrice-like material may be stored and thus made available when the elastomeric material is passed outwardly from its cavity.

In addition, the present invention can be fabricated—if desired—by coaxial concurrent extrusion techniques. If such be the case, an adhesive, as desired, can be included upon the interior wall of the housing, so as to further assist in the drawing down the elongation process within the housing. The adhesive can be applied to the wall of the housing, as part of the extrusion process or to the exterior of the elastomeric-like material. In such case, the dentifrice would be mixed with the elastomeric material.

In another mode of manufacture, the elastomeric-like material may be prefabricated from one or more monofilaments and passed through the extruder, in unextended form, so as to be extruded and formed as part of the outer housing, when it is extruded. Such monofilaments may be of initially large diameter, or a combination of monofilaments twisted together or running parallel together, any of which to be drawn down by the single minor drawhole located adjacent the broken portion of each of the ends of the housing. In this manner, the central-most elastomeric-like material, above described, may be preformed and then drawn down to the appropriate size.

Dentifrice-like materials may include flavorings, such as POLYIFF NO. 16924-00349 TM made by International Flavors and Fragrances, Inc., New York City, N.Y., U.S.A., which may be impregnated into or about the exterior surface of the central- most elastomeric-like material. Similarly, liquids, liquid dentifrice-like materials, such as water based compounds mixed with sorbitol, glycerin, cefyipyridirium chloride, polysorbates, and flavorings and colorings, may be utilized as a liquid, as desired. Gel-like dentifrices, similar to toothpastes, comprising carbopol, sodium lauryl sulfate, keltrol, sodium hydroxide, sodium saccharin, oils, flavorings, colorings, and preservatives, may be utilized as the dentifrice, as desired. Alternatively, simple imitation flavorings, such as cinnamon, may be employed to impart a pleasant taste upon the application of the elongated elastomeric-like material into the user's mouth. Medicaments, utilized alone, or in combination with the foregoing, such as fluoride compounds, other well-known antiseptics, talcs, and lubricants, may be utilized as the dentifrice-like material.

Now referring to the figures, and more particularly to the embodiment illustrated in FIG. 1, showing housing 10 with portions 12 and 14 separated by perforation 15 in the central region of housing 10. Ends 16 and 18 are closed off so as to totally contain elastomeric-like material 20 thereinbetween. Material 20 is admixed to carry a dentifrice-like material.

Figure 2:
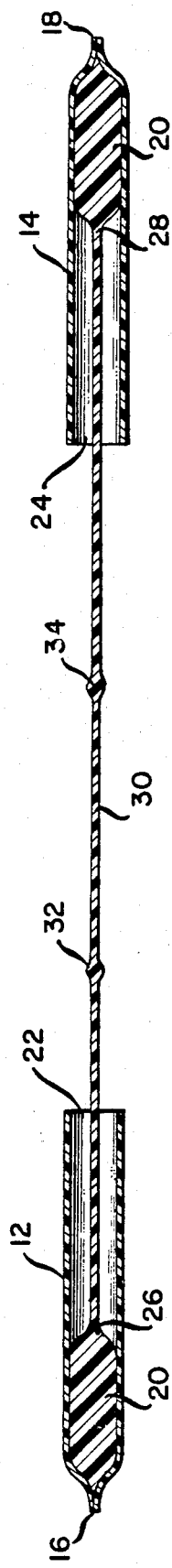
FIG. 2 is a cross-sectional side elevation view of the apparatus shown in FIG. 1, shown when broken and the ends thereof extended apart.

When the apparatus in FIG. 1 is broken, as is shown in FIG. 2, open ends 22 and 24 are disposed opposite each other, whilst material 20 is still engaged within housing ends 12 and 14, in its original shape, excepting in regions 26 and 28 where the extending process has begun. Monofilament-like material 30 is shown opposite intermediate broken ends 22 and 24 and is illustrated having slubs 32 and 34, of larger diameter, which slubs are difficult to remove and create a nuisance in the process of utilizing extended portion 30 in a dental floss-like apparatus.

Figure 3:
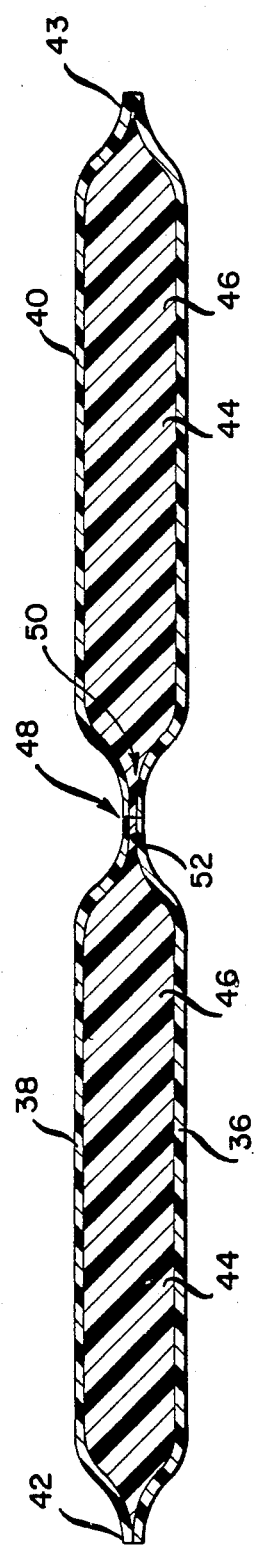
FIG. 3 is a side elevation cross-sectional view of an embodiment of the present invention, shown in its unbroken form.

FIG. 3 illustrates housing 36 comprising ends 38 and 40. As in FIG. 1, oppositemost ends 42 and 43 are closed, so as to form sharpened ends which are suitable as a toothpick-like device, if desired. Contained with housing 36, in the cavity 46 is elastomeric-like material 44. Region 50 is collapsed inwardly, so as to provide for a narrow passageway 52 communicating between housing ends 38 and 40. Region 48 describes the radially inwardly extending region of the housing about passageway 52.

FIG. 4 illustrates the apparatus shown in FIG. 3 when broken adjacent its midregion 50, so as to form broken housing portions 36a and 36b. Drawhole 54 is shown formed in housing 36a, opposite and adjacent drawhole 56, similarly formed in housing 36b. Elastomeric-like material 44, on being tensioned in the direction of arrow 58, has its rightmost end pulled away from interior wall portion 60 of housing 36a. If desired, a layer of adhesive 62 can be formed on the interior wall of housing 36a, to insure a better grasp between elastomeric-like material 44 to housing end 36a. In similar fashion, though not shown, an adhesive may be utilized on the exterior portion of elastomeric-like material portion 46 to secure the interior of housing 36b. Slubs 64 are drawn down to a uniform thickness exposed portion 66. Similarly, drawhole 56 is positioned opposite drawhole 54, and is useful in drawing down, in a uniform fashion, extended material 68, eminating from the elastomeric-like material 46 found in housing 36b.

FIG. 5 illustrates one half of the apparatus shown in FIG. 4, shown in another embodiment. The left-hand housing portion 36a is illustrated showing a thick elastomeric-like material 70 relative to the diameter of drawhole 54a. Extended material 66a is shown as having been formed by passing through drawhole 54a. It should be noted that end 72, of elastomeric-like material 70 is secured to housing 36a, intermediate portions of the housing forming end 42a and drawhole 54a. In this particular embodiment, elastomeric-like material 70 is not adhered to the interior walls of housing 36a, and certainly no adhesive, such as 62 shown in FIG. 4, is required. FIG. 5 may utilize either the same admixed elastomeric-like material or, as shown, utilize the dentifrice-like material 94 covering or adhering to the surface of elastomeric material 70, before and after the elastomeric-like material is partially withdrawn from the housing 96.

FIG. 6 illustrates elastomeric-like material 70, as shown in FIG. 5, having a uniform large cross-section.

FIGS. 7 & 7A illustrate a multistranded monofilament 74 in combination, being of rope-like construction, shown in cross-section utilizable instead of unitary material 70, shown in FIG. 5. Cells 98 are shown depicting blown openings in elastomeric-like material 70, in which the dentifrice-like material 94 is stored. Alternately, elastomeric-like material 70 may be admixed with dentifrice-like material, as in FIG. 1, if desired.

In this embodiment, and applicable to the embodiment shown in FIG. 5, liquid-like or gel-like dentifrice material 104 is carried within housing 78, and is free for dispensation covering or simultaneously admixing with extrudate 88 upon the extrusion of extrudable material 88 outwardly from housing 84.

The interior of housings 12, 14, 36, 36a, 36b, 38, 40, and 78 may be coated with a non-porous, impervious coating or fabricated from a non-porous, impervious material to eliminate or control evaporation and spoilage, prior to use.

FIGS. 8 & 8A comprise monofilaments 76, similarly prefabricated prior to the extrusion process. Monofilaments 76 extend parallel to one another when enclosed within housing ends 36a and 36b. Monofilaments 76 may have cells 102 thereon, similar to cells 98, carrying dentifrice-like material 94.

FIG. 9 illustrates another embodiment of the invention shown in side elevation, cross-sectional view in which half a portion of the housing 78 is shown having closed end 80. Closed end 80 may, if desired for cosmetic purposes, be sealed in a tapered fashion, not shown, so as to present a clean appearance and to be useful as a toothpick—if so desired.

Depression area 82 is shown intermediate end 80 and end 84 of this embodiment. End 84 contains drawhole 86 from which stretched strongest elongatable material 88 emerges for use, carrying dentifrice 106, previously stored in housing 78, and identified as 104 therein. The depressed area 82 is used as a technique to secure a portion of monofiliment 90 to handle housing end 78, without employing an adhesive therefor. Another great advantage of this embodiment is that only a coated portion 92 of elongatable material 90 can be permitted to be extended. The length of tensile material 88 is controlled by the bulk of unextended material 92 or, in other words, the distance separating depression 82 and drawhole 86.

It should be remembered that the process which closes ends 42 and 43, shown in FIGS. 3 and 4, utilizes a heat and pressure application, in a technique well known in the art. Similarly, the circular inward depression 48, shown in FIG. 3, is formed utilizing pressure with or without heat, so as to result in draw down holes 54 and 56 and a region of the housing which is defined to be broken.

One of the advantages of the present invention is a one-time use dentifrice-carrying dental flossing device which does not require manual manipulation of the dental floss-like material, as by contacting same with the user's hand, prior to its use.

Another advantage of the present invention is a dentifrice-carrying dental floss-like housing which housing maintains the flossing material in a clean, safe and undisturbed condition following its initial manufacture, which permits the user to easily and quickly make a clean dental floss-like material readily available for use.

Still another advantage of the present invention is an inexpensive dentifrice storage device, using a dental flossing device which in of itself, may be carried about, from place to place, such that the integrity of the cleanliness of the dental floss and dentifrice is not harmed prior to the time in which the user elects to utilize same.

Yet another advantage of the present invention is a dentifrice and dental flossing device which is simple to manufacture, convenient in its use, rugged in its construction, and which may bear advertising or other descriptive material directly thereupon.

A further advantage of the present invention is overcoming the objectional concept of requiring users to put their fingers into their mouths when utilizing a dental floss-like device.

Still yet another advantage of the present invention is avoiding the need for the user to wind the dental floss about their fingers, prior to the use thereof.

Still a further advantage of the present invention is utilizing a dental floss-like material which reaches a uniform cross-section at its elongated length, which will not extend further, whilst having a uniform cross-section throughout its exposed length, thereby making it more convenient to utilize the apparatus.

Yet another advantage of the present invention is a dental floss device which dispenses dentifrice and dental floss-like material, without spoilage or evaporation prior to use.

The present invention utilizes a housing of any desired shape. The housing includes a cavity. Within the cavity there resides an elastomeric-like material which stretches and when reaching a certain length, increases its tensile strength substantially, without possessing the characteristic of reverting to its initial cross-section or snapping back. As desired, such material may be admixed or coated with a dentifrice-like mixture or simply containing said mixture. The cavity housing, defining the cavity, when broken about a weakened or defined portion, separates the cavity into two ends. Opposite and adjacent these ends, and formed by the housing are two small draw down holes, whose cross-sectional dimensions are substantially smaller than the internal diameter of the housing. The elastomeric-like material is secured to the closed ends of the housing, located furthest most from each other and opposed from the draw down holes. The elastomeric-like material may be adhered to the sidewalls of the housing, either by the use of an adhesive or not, or may be formed from the elastomeric-like material having a cross-section equal to or somewhat smaller than the internal dimensions of the housing, or may be fabricated from pre-extruded monofilaments which are joined together either by twisting or running parallel to one another or simply having a cross-section whose dimensions are greater than the draw down holes formed at the location of the broken ends of the housing. In the case of the smaller diameter cross-section, the dentifrice may totally or partially fill the balance of the internal diameter of the housing.

Thus, there is disclosed in the above description and in the drawings, an embodiment of the invention which fully and effectively accomplishes the objects thereof. However, it will become apparent to those skilled in the art, how to make variations and modifications to the instant invention. Therefore, this invention is to be limited, not only by the specific disclosure herein, but by the appending claims.

The embodiment of the invention in which an exclusive privilege or property is claimed are defined as follows; I claim:

1. An oral hygiene device comprising a unitary housing, said housing defining a cavity therewithin, means to separate said housing into at least two portion, a flexible elongatable material, said material being capable of being permanently elongated once said material is stretched, said material being disposed within said cavity when un-elongated, said material having a pair of ends, one said pair of ends being secured within said cavity to one of said at least two portions of said housing, the other of said pair of ends being secured within said cavity to another of said at least two portions of said housing, said material being elongatable so as to have an exposed length equal to the spaced apart distance separating each said pair of ends when housing is separated into said at least two portions and disposed spaced apart from one another, said housing having two openings therein, said two openings having cross-sectional dimensions substantially smaller than the cross-sectional dimensions of the interior portions of each of said housing portions, said two openings being disposed substantially at the location formed in each of said pair of ends adjacent and opposite each other when said housing is separated into said spaced apart relationship, said flexible elongatable material passing through both said two openings when said housing is in unitary form and when said housing is separated into said at least two portions, a dentifrice-like material residing within said cavity, said dentifrice-like material covering said elongatable material before said housing is separated into said at least two portions, means to dispense said dentifrice-like material outwardly from said cavity when said housing is separated into said at least two portions.

2. The appaaratus as claimed in claim 1 further comprising means whereby said dentifrice-like material is fully contained within said cavity until said cavity is broken into said at least two portions.

* * * * *